(12) United States Patent
Oda et al.

(10) Patent No.: US 7,141,650 B2
(45) Date of Patent: Nov. 28, 2006

(54) CAP-BINDING PROTEIN

(75) Inventors: Tamaki Oda, Tsukuba (JP); Hideki Endoh, Tsukuba (JP); Yoshitaka Ueda, Tsukuba (JP); Kazunori Inabe, Tsukuba (JP)

(73) Assignee: Astellas Pharma, Inc., Tokyo (JP)

( * ) Notice: Subject to any disclaimer, the term of this patent is extended or adjusted under 35 U.S.C. 154(b) by 0 days.

(21) Appl. No.: 10/530,886

(22) PCT Filed: Oct. 9, 2003

(86) PCT No.: PCT/JP03/12968

§ 371 (c)(1),
(2), (4) Date: Apr. 11, 2005

(87) PCT Pub. No.: WO2004/033688

PCT Pub. Date: Apr. 22, 2004

(65) Prior Publication Data

US 2006/0008857 A1    Jan. 12, 2006

(30) Foreign Application Priority Data

Oct. 11, 2002    (JP) .............................. 2002-298549

(51) Int. Cl.
*A61K 14/00*    (2006.01)
(52) U.S. Cl. .................................................... 530/350
(58) Field of Classification Search ................. 530/350
See application file for complete search history.

(56) References Cited

FOREIGN PATENT DOCUMENTS

WO    WO 03/23002 A2    3/2003

OTHER PUBLICATIONS

GENBANK: BQ070301—Apr. 2, 2002.*
Sequence alignment, BQ070301 and Seq Id No. 2.*
Bowie et al. Deciphering the Message in Protein Sequences: Tolerance of Amino Acid Substitutions. Science. 1990. vol. 247, pp. 1306-1310.*
Wells J.A. Additivity of Mutational Effects in Proteins. Biochemistry. 1990. vol. 29, No. 37, pp. 8509-8517.*
Strausberg et al. Generation and Initial Analysis of More Than 15,000 Full-length Human and Mouse cDNA Sequences. Proceedings of the National Academies of Sciences, U.S.A. Dec. 2002. vol. 99, No. 26, pp. 16899-16903.*
Cronshaw et al. Proteomic Analysis of the Mammalian Nuclear Pore Complex. The Journal of Cell Biology. Sep. 2002. vol. 158, No. 5, pp. 915-927.*
J. M. Cronshaw et al., "Proteomic analysis of the mammalian nuclear pore complex", (2002) J. Cell. Biol., vol. 158, No. 5, pp. 915-927.
International Search Report dated Nov. 26, 2003.
Database EMBL [Online] Apr. 4, 2002, "AGENCOURT_6860769 NIH_MGC_47 Homo sapiens cDNA clone IMAGE:5922671 5', mRNA sequence." XP002376217 retrieved from EBI accession No. EM_EST:BQ070301 Database accession No. BQ070301.
Liu, Jun, et al., "APS facilities c-Cbl tyrosine phosphorylation and GLUT4 translocation in repsonse to insulin in 3T3-L1 adipocytes", Molecular and Cellular Biology, vol. 22, No. 11, Jun. 2002, pp. 3599-3609.

* cited by examiner

*Primary Examiner*—Jon Weber
*Assistant Examiner*—Suzanne M. Noakes
(74) *Attorney, Agent, or Firm*—Sughrue Mion, PLLC (57) ABSTRACT

A novel polypeptide which is useful in screening of an agent for improving insulin resistance and an agent for improving glucose metabolism, a polynucleotide encoding the polypeptide, an expression vector comprising the polynucleotide, and a cell transformed with the expression vector are disclosed. The polypeptide is a protein expressed in skeletal muscle. When the protein is overexpressed, incorporation of sugar into a cell is inhibited.

A method for screening of an agent for improving insulin resistance and/or an agent for improving glucose metabolism in which the polypeptide is used, and a method for producing a pharmaceutical composition for insulin resistance and/or glucose metabolism improvement comprising a substance obtained according to the method for screening as an active ingredient are also disclosed.

5 Claims, 1 Drawing Sheet

CAP-BINDING PROTEIN

TECHNICAL FIELD

The present invention relates to a novel polypeptide which binds to c-Cbl-associated protein (CAP), a novel polynucleotide encoding the polypeptide, a vector comprising the polynucleotide, and a transformed cell containing the vector.

BACKGROUND ART

Insulin is secreted from β cells of pancreatic Langerhans islet, and lowers the blood sugar level by predominantly acting on muscle, liver and fat to allow sugar in blood to be incorporated into the cell, stored therein, and consumed. Diabetes is caused by insufficient function of the insulin, and there are two types of patients, i.e., type 1 having disorder in production and/or secretion of insulin, and type 2 having difficulty in acceleration of sugar metabolism by insulin. In either patient, blood sugar level is higher than that in healthy people. However, blood insulin is absolutely deficient in the type 1, while insulin resistance is developed in which the incorporation and consumption of blood sugar is not accelerated irrespective of the presence of insulin in the type 2. Type 2 diabetes is the so-called life-style related disease, which results from overfeeding, lack of exercise, stress and the like in addition to hereditary predisposition. In these days, the type 2 diabetic patients have increased rapidly as the caloric intake is elevated in advanced nations, and in Japan, such patients account for 95% of the diabetic patients. Thus, therapeutic drugs for diabetes should not only be simple hypoglycemic agents, but the necessity of studies of therapy targeted to type 2 diabetes has increased in which glucose metabolism is accelerated through the improvement of insulin resistance.

Currently, for the therapy of type 1 diabetic patients, an insulin injection formulation is prescribed. On the other hand, examples of known hypoglycemic agents prescribed for type 2 diabetic patients include: sulfonylurea hypoglycemic agents (SU agents) which act on pancreatic β cells to accelerate secretion of insulin; biguanide hypoglycemic agents having activity to increase utilization of sugar by anaerobic glycolytic activity, to suppress gluconeogenesis, and to suppress intestinal absorption of sugar; as well as α-glucosidase inhibitors which retard digestion and absorption of carbohydrates, in addition to insulin injection formulations. Although these agents indirectly improve insulin resistance, thiazolidine derivatives have been used as agents which directly improve insulin resistance, in recent years. Its activity is to incorporate glucose into the cells, and to accelerate utilization of the glucose within the cells. The thiazolidine derivative has been demonstrated to act as an agonist of peroxisome proliferator activated receptor gamma (PPARγ) (nonpatent document 1). However, the thiazolidine derivative has been known to exhibit not only the improving effect on insulin resistance but a side effect to cause edema (nonpatent documents 2–3). Since the induction of edema is a serious side effect which results in cardiac hypertrophy, for the purpose of the improvement of insulin resistance, useful target molecules for development of new drugs which can be an alternative to PPARγ have been desired.

Signal of the insulin function is transduced into a cell via an insulin receptor on the cell membrane. In the action pathway of insulin, there are two pathways, i.e., first and second pathways (nonpatent document 4). In the first pathway, the signal is sequentially transduced from the activated insulin receptor via IRS-1 and IRS-2, PI3 kinase, PDK1 to Akt1 (PKBα) or Akt2 (PKBβ), or PKCλ or PKCζ. As a result, incorporation of sugar from outside of the cell is accelerated by translocating a glucose transporter GLUT4, which is present within a cell, onto the cell membrane (nonpatent document 5). On the other hand, in the second pathway, the signal is sequentially transduced from the insulin receptor via c-Cbl and CAP to CrK II, C3G and TC10, and consequently, the incorporation of sugar by GLUT4 is accelerated (nonpatent document 6). However, details of the insulin signal transduction pathway are still unclear in part, and particularly, it is not clear which mechanism is finally involved in these signals to accelerate the cellular incorporation of sugar via the glucose transporter.

CAP is an adaptor protein which exists in the second pathway of the insulin signaling, and is highly expressed in liver, skeletal muscle, kidney and heart which are insulin sensitive tissues (nonpatent document 7). Furthermore, the expression of CAP has been known to be enhanced by a thiazolidine derivative which is a PPARγ agonist (nonpatent document 8). CAP binds to c-Cbl via an SH3 domain at its C-terminal side. The CAP/c-Cbl complex responds to the insulin signal, thereby activating TC10 via a CrkII-C3G complex to accelerate the translocation of the glucose transporter GLUT4 to the cell membrane. It was reported that although CAP having deficiency of SH3 which is a binding domain to c-Cbl (CAP ΔSH3) does not affect the PI3 kinase activity, it inhibits cellular incorporation of sugar (nonpatent document 9). From these findings, it is believed that CAP is a signal mediating factor which acts in incorporation of sugar into cells depending on the binding to c-Cbl, and that the inhibition of its function may result in insulin resistance through partial blocking of insulin signal transduction, thereby causing type 2 diabetic pathologic conditions.

Patent Document 1
Pamphlet of International Publication No. 01/75067

Patent Document 2
Specification of U.S. patent Publication No. 2002/0119919

Patent Document 3
Pamphlet of International Publication No. 00/58473

Nonpatent Document 1
*The Journal of Biological Chemistry*, (USA), 1995, Vol. 270, pp. 12953–12956

Nonpatent Document 2
*Diabetes Frontier*, (USA), 1999, Vol. 10, pp. 811–818

Nonpatent Document 3
*Diabetes Frontier*, (USA), 1999, Vol. 10, pp. 819–824

Nonpatent Document 4
*The Journal of Clinical Investigation*, (USA), 2000, Vol. 106, No. 2, pp. 165–169

Nonpatent Document 5
*The Journal of Biological Chemistry*, (USA), 1999, Vol. 274, No. 4, pp. 1865–1868

Nonpatent Document 6
*Nature*, (United Kingdom), 2001, Vol. 410, No. 6831, pp. 944–948

Nonpatent Document 7
*Molecular and Cellular Biology*, (USA), 1998, Vol. 18, No. 2, pp. 872–879

Nonpatent Document 8

*The Journal of Biological Chemistry*, (USA), 2000, Vol. 275, No. 13, pp. 9131–9135

Nonpatent Document 9

*The Journal of Biological Chemistry*, (USA), 2001, Vol. 276, No. 9, pp. 6065–6068

Nonpatent Document 10

*Molecular and Cellular Biology*, (USA), 2002, Vol. 22, No. 11, pp. 3599–3609

DISCLOSURE OF THE INVENTION

The inventors of the present invention thought that insulin resistance can be improved if the activity of CAP is enhanced, based on the findings described above. In addition, it was conceived that this object can be accomplished by identifying an intracellular factor which binds to CAP, which is an adaptor protein, and controls the action of CAP, whereby regulating the action thereof. Accordingly, the inventors of the present invention identified a protein which binds to CAP by a yeast two-hybrid system. Consequently, a cDNA derived from human having a novel nucleotide sequence encoding a protein CAPBP1 (CAP binding protein 1), which is expressed in skeletal muscle that is an insulin responsive tissue, was successfully cloned. Moreover, it was found that the protein is a causal factor of a diabetic pathologic condition on the basis of the findings: that the expression level of the mouse orthologue of the protein in muscle tissues of a diabetic model mice is remarkably increased compared to that in normal individuals; that when the protein is overexpressed in adipocytes, incorporation of sugar into the cell is inhibited; and that the protein interacts with GSK3 protein which is a kinase and inactivates glycogen synthase. The inventors of the present invention hereby provide a novel polypeptide which is useful for screening of an agent for improving insulin resistance and/or an agent for improving glucose metabolism, a polynucleotide encoding the polypeptide, an expression vector comprising the polynucleotide, a cell transformed with the expression vector, a method for screening of an agent for improving insulin resistance and/or an agent for improving glucose metabolism, and a method for the production of a pharmaceutical composition for improving insulin resistance and/or improving glucose metabolism, and thus, the present invention was accomplished.

Accordingly, the present invention relates to:

[1] A polypeptide which comprises the amino acid sequence represented by SEQ ID NO:2 or 4, and binds to CAP; or a polypeptide which consists of an amino acid sequence in which 1 to 10 amino acids are deleted, substituted, and/or inserted in the amino acid sequence represented by SEQ ID NO:2 or 4, and binds to CAP.

[2] A polypeptide which consists of an amino acid sequence having a homology of 90% or more with the amino acid sequence represented by SEQ ID NO:2 or 4, and is a protein which binds to CAP.

[3] A polypeptide consisting of the amino acid sequence represented by SEQ ID NO:2 or 4.

[4] A polynucleotide encoding the polypeptide according to any one of [1] to [3].

[5] An expression vector comprising the polynucleotide according to [4].

[6] A cell transformed with the expression vector according to [5].

[7] A method for screening a binding inhibitor between the polypeptide according to any one of [1] to [3] and CAP, which comprises:

allowing the polypeptide to contact with a test substance, measuring change of binding between the polypeptide and CAP, and selecting a substance which inhibits the binding.

[8] The method for screening according to [7], wherein the binding inhibitor is an agent for improving insulin resistance and/or an agent for improving glucose metabolism.

[9] A method for screening an agent for improving insulin resistance and/or an agent for improving glucose metabolism, which comprises:

allowing a cell which expresses the polypeptide according to any one of [1] to [3] to contact with a test substance, and measuring change of the expression amount of the polypeptide.

[10] A method for producing a pharmaceutical composition for improving insulin resistance and/or improving glucose metabolism, which comprises:

carrying out screening with the method for screening according to any one of [7] to [9], and carrying out formulation using the substance obtained by the screening.

Nucleotide sequences having a homology to the polynucleotide of the present invention are disclosed in patent document 1 to patent document 3. In the patent document 1 and patent document 3, numerous nucleotide sequences are disclosed as well as the sequence of 1137 bases or 1515 bases including the sequence having a homology to the polynucleotide of the present invention. Although it is described that all of them can be used in diagnosis and screening, no specific use of individual ones is described. Patent document 2 discloses numerous nucleotide sequences, and among them, a sequence of 32204 bases comprising the sequence having a homology to the polynucleotide of the present invention is disclosed. Although it is described to be involved in many diseases, particularly alimentary diseases, any experimental support is not shown. Sequences having a homology to the polynucleotide and polypeptide of the present invention are described as Accession No. AF514992 in the sequence database of GenBank and GenPept, however, specific use thereof is not described. Furthermore, the patent document 3 discloses sequences having a homology to the polypeptide of the present invention, and it is described that many sequences can be used for diagnosis and screening, similarly to the aforementioned polynucleotide. However, specific use of individual ones is not described at all. In addition, WO 03/023002 pamphlet which was published after the priority date of the application discloses numerous sequences comprising sequences having a homology to the polypeptide and polynucleotide of the present invention, and discloses many names of diseases including diabetes as diseases in which they may be involved. However, there is not any specific description of obtaining these sequences actually, and any experimental support of the use is not found at all. Therefore, the inventors of the present invention found the polypeptide and polynucleotide of the present invention for the first time and elucidated that increase in the protein accounts for the diabetic pathologic condition for the first time. Additionally, the method for screening according to the present invention in which binding between the polypeptide of the present invention and CAP is utilized is found by the inventors of the present invention for the first time.

BEST MODE FOR CARRYING OUT THE INVENTION

The present invention will be explained in detail below.

The polypeptide and polynucleotide of the present invention, which have a property to bind to CAP, and which increase in their amount of expression in diabetic conditions, is useful in diagnosis of diabetes. Also, the polypeptide, the polynucleotide, the expression vector and the cell of the present invention are useful in screening of an agent for treating diabetes. Diagnosis of diabetes is enabled by utilizing a primer for PCR which can detect the polynucleotide of the present invention.

<Polypeptide of the Present Invention>

The polypeptides according to the present invention include:

(1) a polypeptide consisting of the amino acid sequence represented by SEQ ID NO:2 or 4;

(2) a polypeptide which comprises the amino acid sequence represented by SEQ ID NO:2 or 4, and which binds to CAP, or a polypeptide consisting of an amino acid sequence in which 1 to 10 are deleted, substituted, and/or inserted (preferably 1 to 7, more preferably 1 to 5, and still more preferably 1 to 3) amino acids in the amino acid sequence represented by SEQ ID NO:2 or 4, and which binds to CAP (hereinafter, referred to as functional equivalent modified product); and (3) a polypeptide which consists of an amino acid sequence having a homology of 90% or greater to the amino acid sequence represented by SEQ ID NO:2 or 4, and which is a protein which binds to CAP (hereinafter, referred to as homologous polypeptide).

The homologous polypeptide of the present invention is not particularly limited as long as it consists of an amino acid sequence having a homology of 90% or more with the amino acid sequence represented by SEQ ID NO:2 or 4, and is a polypeptide which binds to CAP, and is preferably, a polypeptide consisting of an amino acid sequence having a homology of preferably 95% or more, and still more preferably 98% or more with the amino acid sequence represented by SEQ ID NO:2 or 4 is preferred. For reference, the term "homology" in the present specification means the value of identities obtained using a parameter provided by default according to the search on Clustal Program (Higgins and Sharp, *Gene* 73, 237–244. 1998; Thompson et al. *Nucl. Acids Res.* 22, 4673–4680, 1994). The parameters are described as follows:

K tuple 1
Gap Penalty 3
Window 5
Diagonals Saved 5 as Pairwise Alignment Parameters.

Moreover, the polypeptide of the present invention also includes those derived from other vertebrates (for example, mouse, rat, rabbit, horse, sheep, dog, monkey, cat, bear, pig, chicken and the like).

<Polynucleotide of the Present Invention>

The polynucleotide of the present invention may be any one of the nucleotide sequences coding for the polypeptide of the present invention, i.e., a polypeptide represented by the amino acid sequence represented by SEQ ID NO:2 or 4, a functional equivalent modified product thereof, or a homologous polypeptide thereof. Additionally, the polynucleotide may be derived from any species. Preferably, it is a polynucleotide consisting of a nucleotide sequence encoding the amino acid sequence represented by SEQ ID NO:2 or 4, and more preferably, it is a nucleotide sequence represented by SEQ ID NO:1 or 3. In addition, the "polynucleotide" in the present specification may include both DNA and RNA.

The polynucleotide of the present invention can include all mutants as long as it codes for the polypeptide of the present invention. More specifically, naturally occurring allelic mutants, mutants which are not naturally occurring, mutants having deletion, substitution, addition and insertion can be included. The mutant may be, for example, generated by mutation in nature, or may be artificially modified or produced. The present invention includes all mutant genes encoding the polypeptide of the present invention irrespective of causes and means for the mutation of the polynucleotide. Artificial methods leading to production of the mutant as described above include, for example, genetic engineering procedures such as base specific substitution methods (*Methods in Enzymology*, (1987) 154, 350, 367–382), as well as chemical synthetic means such as phosphoric acid triester methods and amidide phosphate method (*Science* (1968) 150, 178). By combination of these, a DNA accompanied by desired base substitution can be obtained. Alternatively, causing substitution of nonspecified base in a DNA molecule is enabled by repeating operation of a PCR method, or allowing manganese ion or the like to exist in the reaction liquid.

The polynucleotide and polypeptide of the present invention can be easily produced and obtained by a general genetic engineering procedure on the basis of the sequence information disclosed according to the present invention.

The polynucleotide encoding the polypeptide of the present invention can be obtained, for example, as follows, and is not limited thereto. Also, it can be obtained by a known procedure as in "*Molecular Cloning*", Sambrook, J. et al., Cold Spring Harbor Laboratory Press, 1989.

For example, (1) a mehtod in which PCR, (2) a method in which general genetic engineering procedure (i.e., a process of selecting a transformed strain which includes a desired amino acid among transformed strains which was transformed with a cDNA library), or (3) a chemical synthesis process can be illustrated. Each method for the production can be carried out similarly to that described in WO 01/34785.

In the process in which PCR is utilized, the polynucleotide described in the present specification can be produced according to the procedure described in, for example, 1) production mehtod of protein gene, a) first production method in "Mode for Carrying Out the Invention" of the above patent document. In the description, examples of the "human cell or tissue having an ability to produce the protein of the invention" include e.g., human skeletal muscle. mRNA is extracted from human skeletal muscle. Then, a reverse transcriptase reaction is carried out with the mRNA in the presence of a random primer or an oligo dT primer to synthesize a first strand cDNA. Thus the resulting first strand cDNA is subjected to a polymerase chain reaction (PCR) using two kinds of primers having a partial region of interposing the intended gene interposed, thereby capable of obtaining the polynucleotide of the present invention or a part thereof. More specifically, for example, the polynucleotide of the present invention can be produced according to the method described in Example 1.

In the method in which a routine genetic engineering procedure is used, for example, the polynucleotide encoding the polypeptide of the present invention can be produced according to the procedure described in, for example, 1) production method of protein gene, b) second of the production method in "Mode for Carrying Out the Invention" of the above patent document.

In the process in which a chemical synthesis mehtod is utilized, for example, the polynucleotide encoding the polypeptide of the present invention can be produced according to the procedure described in, for example, 1) production method of protein gene, c) third production mehtod, or d) fourth production method in "Mode for Carrying Out the Invention" of the above patent document.

Through utilizing the resulting partial or entire nucleotide sequence of the polynucleotide of the present invention, the expression level of the polynucleotide of the present invention in individuals or various tissues can be specifically detected.

Examples of method of such detection include methods of RT-PCR (Reverse transcribed-Polymerase chain reaction), Northern blotting analysis, in situ hybridization and the like. Primer for use in detecting the polynucleotide encoding the polypeptide of the present invention by RT-PCR is not particularly limited as long as it can specifically amplify the polynucleotide alone, and it can be determined appropriately based on the sequence information of the polynucleotide of the present invention. The primer which specifically amplifies the polynucleotide of the present invention can be utilized as a specific primer and a specific probe for detecting the polynucleotide of the present invention.

<Expression Vector and Cell of the Present Invention>

The polynucleotide encoding the polypeptide of the present invention obtained as described above can be utilized for the expression of the polypeptide of the present invention in vitro, or in test cells by ligating downstream of an appropriate promoter according to the method described in "*Molecular Cloning*" (Sambrook, J. et al., Cold Spring Harbor Laboratory Press, 1989) and the like.

Specifically, addition of the polynucleotide encoding the polypeptide of the present invention obtained as described above to downstream of a polynucleotide including a particular promoter sequence enables the expression of the polypeptide of the present invention by means of gene transcription and translation in a cell free system using this product as a template.

Alternatively, when the polynucleotide encoding the polypeptide of the present invention described above is incorporated into an appropriate vector plasmid followed by the introduction in the form of a plasmid into a host cell, the expression of the polypeptide of the present invention in the cell is enabled. Otherwise, a cell having a chromosomal DNA with such a construction incorporated therein may be obtained, and used. More specifically, a fragment including an isolated polynucleotide can transform eukaryotic and prokaryotic host cells through the incorporation into an appropriate vector plasmid again. Moreover, through introducing an appropriate promoter and a sequence involved in phenotypic expression into such vector, the expression of the polypeptide of the present invention is permitted in each host cell. The host cell is not particularly limited and it may be any one as long as detection of the amount of expression of the polypeptide of the present invention is enabled at the messenger RNA level, or at the protein level. It is more preferred that a fat-derived cell, or a muscle-derived cell which is rich in endogenous CAP is used as the host cell.

Process for transforming the host cell to allow the gene to be expressed can be carried out according to the method described in, for example, 2) production method of vector of the present invention, host cell of the present invention, recombinant protein of the present invention in "Mode for Carrying Out the Invention" of the above patent document. The expression vector is not particularly limited as long as a desired polynucleotide is included. Examples of the vector include an expression vector obtained by inserting a desired polynucleotide into a known expression vector selected appropriately depending on the host cell. The cell of the present invention can be obtained by, for example, transfecting a desired host cell with the aforementioned expression vector. More specifically, an expression vector of a desired protein can be obtained by, for example, incorporating a desired polynucleotide into an expression vector pcDNA 3.1 in mammalian animal cells as described in Example 2, and the transformed cell of the present invention can be produced by allowing the expression vector to be incorporated into COS-1 cells using a lipofectamine reagent.

The desired transformed cell obtained as described above can be cultured according to a common procedure, and the desired protein is produced by the culture. As the medium used for the culture, any type may be selected appropriately which is commonly used depending on the host cell employed. For example, in cases of the COS-1 cell, Dulbecco's modified Eagle minimum essential medium (DMEM) supplemented with a serum component such as fetal bovine serum (FBS) to which G418 is added can be used.

By culturing the cell of the present invention, the polypeptide of the present invention produced in the cells can be detected, quantitatively identified, and furthermore, purified. The polypeptide of the present invention can be detected and purified by, for example, a Western blotting method or immunoprecipitation method wherein an antibody which binds to the polypeptide of the present invention is used. Alternatively, through allowing the polypeptide of the present invention to be expressed as a fusion protein with an appropriate tag protein such as glutathione-S-transferase (GST), protein A, β-galactosidase or maltose-binding protein (MBP), the polypeptide of the present invention can be detected by a Western blotting method or immunoprecipitation method using a specific antibody to the tag protein, and can be purified utilizing the tag protein. Otherwise, the purification can be also carried out by any of various separation methods utilizing a physical property or chemical property of the protein, if desired. Specifically, utilization of ultrafiltration, centrifugation, gel filtration, affinity chromatography, ionic exchange chromatography, affinity chromatography or high performance liquid chromatography can be used.

The polypeptide of the present invention can be produced according to a common chemical synthesis procedure on the basis of the amino acid sequence information represented by SEQ ID NO:2 or 4. Specifically, peptide synthesis procedures by liquid phase and solid phase method may be included. Upon the synthesis, amino acids may be serially bound one by one, or may be bound after synthesizing a peptide fragment consisting of several amino acids. The polypeptide of the present invention obtained in such a manner can be purified according to any one of various methods described above.

<Method for Screening of the Present Invention>

A method for screening of a substance having an activity to improve glucose metabolism can be constructed using the polypeptide of the present invention, in which change of binding between CAP and c-Cbl is used as a marker utilizing the interaction of the polypeptide of the present invention with CAP.

It was revealed that the polypeptide of the present invention negatively controls the insulin signal via the binding with CAP from the findings that: CAPBP1 which is one of the polypeptides of the present invention binds to CAP; expression of the mouse orthologue is enhanced in diabetic model mice; and incorporation of sugar is inhibited in adipocytes in which overexpression of CAPBP1 is allowed. Therefore, screening of an agent for improving insulin resistance and/or an agent for improving glucose metabolism can be carried out by the aforementioned method for screening.

In one embodiment of the method for screening as described above, a method for screening of a substance having an activity to improve glucose metabolism is provided in which a test cell expressing a part or full length region of the polypeptide of the present invention is used, followed by allowing the test cell to coexist with a test substance, and then quantitative or qualitative change of binding between CAP and c-Cbl caused by the test substance in the test cell is used as a marker.

The test substance for use in the method for screening of the present invention is not particularly limited, and includs such as commercially available compounds including peptides, various known compounds entered in Chemical File including peptides, compounds obtained by combinatorial chemistry techniques (N. Terrett et al., *Drug Discov. Today*, 4 (1):41, 1999), culture supernatants of microorganisms, natural elements derived from plants or marine organisms, extracts of animal tissues, or chemically or biologically modified compounds including peptides of the compounds including peptides selected by the method for screening of the present invention.

Although the method for screening as described above is not particularly limited, specifically, the following methods for screening are shown.

1) Method for Screening in Which Binding between the Polypeptide of the Present Invention and CAP is Utilized Since the polypeptide of the present invention negatively controls the insulin signal via the binding to CAP, the following method for screening is used in which binding between the polypeptide of the present invention and CAP is used as a marker. Specifically, a test cell expressing a part or full length region of the polypeptide of the present invention, or a part or full length region of the polypeptide of the present invention fused to a tag such as GST, Flag or HIS is treated or not treated with a test substance. The test cells are preferably cells responsive to insulin, and more specifically, adipocytes, hepatic cells, or cells derived from skeletal muscle are preferred. Immunoprecipitation of the cell using an anti-CAP antibody enables concentration of the CAP protein and the protein bound thereto. It is desired that the same test substance as that used for the treatment of the cell described above is included in the reaction liquid in this concentration step. The concentrated liquid of the CAP and the binding protein thereof is separated by a polyacrylamide gel electrophoresis method according to a known process, and then, the amount of the polypeptide of the present invention is measured by Western blotting using an antibody. Accordingly, a test substance which inhibits the binding between the polypeptide of the present invention and CAP can be selected. Examples of the antibody which may be used herein include antibodies to the polypeptide of the present invention produced with the polypeptide of the present invention or a partial sequence thereof (for example, anti-CAPBP1 antibodies), or antibodies that recognize the tag. Furthermore, similarly to the process described above, a test substance which inhibits the binding between CAP and the polypeptide of the present invention can be also selected by combination of in vitro pulldown method in which a CAP protein purified through tagging such as GST is used (Experimental engineering (Zikken Kogaku), Vol. 13, No. 6. 1994, pp. 528, Matsushime et al.) from the cell extract expressing the polypeptide of the present invention to which a test substance is or is not added and similar Western blotting to that described above. Alternatively, without using a cell extract expressing the polypeptide of the present invention, a test substance which inhibits the binding between CAP and the polypeptide of the present invention (for example, CAPBP1) can be similarly selected also in cases where a protein mixture produced by direct in vitro transcription and translation of a protein which is the polypeptide of the present invention (for example, CAPBP1 protein) using a TNT kit (Promega Corporation) from an expression plasmid of the polypeptide of the present invention (for example, CAPBP1 expression plasmid produced in Example 1 (5)), to which a test substance is or is not added is used. According to any one of these methods, screening of many test substances is enabled by carrying out known spot Western blotting without using a polyacrylamide electrophoresis method. Also, screening to select a test substance which inhibits binding between CAP and the polypeptide of the present invention is possible according to a known ELISA method which comprises adding a test substance to a cell lysate in which the polypeptide of the present invention following the fusion with a tag and CAP are expressed at the same time. Furthermore, utilizing a two-hybrid system (Clontech) in a known mammalian cell, a test substance that inhibits the binding between CAP and the polypeptide of the present invention can be screened and selected from a large population through arranging CAP fused to a DNA binding region of GAL4 as a bait and the polypeptide of the present invention fused to a transcription promoting region of VP16 on the prey side, by the detection of preexisting CAT or a luciferase activity.

2) Method for Screening in which Measurement of the Expression Amount of the Polypeptide of the Present Invention is Utilized The method for screening of an agent for improving insulin resistance and/or an agent for improving glucose metabolism may include a method for screening by the measurement of the expression amount of the polypeptide of the present invention, in addition to the method described in the above paragraph (1). From the findings that expression of the mouse orthologue of CAPBP1 is promoted in diabetic model mice (Example 4) and that incorporation of sugar in the adipocytes overexpressing CAPBP1 is decreased (Example 6), a test substance is expected to have an activity to improve insulin resistance when the expression amount of endogenous CAPBP1 can be reduced by the test substance. Specifically, such substance can be selected by the following method.

First, RNA can be prepared from a cell treated or not treated with a test substance, according to the method demonstrated in Example 4 (1). The cells are preferably cells responsive to insulin, and more specifically, adipocytes, hepatic cells, or cells derived from skeletal muscle are preferred. After separating the RNA by agarose gel electrophoresis from liquid of the RNA preparation according to a known method, it is transferred to a nitrocellulose membrane, which is analyzed by a Northern blotting analysis using a labeled short-chain DNA probe including a sequence of the polynucleotide of the present invention, whereby detection of the change of the expression amount of RNA having a sequence of the polynucleotide of the present invention caused by the test substance is enabled. Accordingly, screening of a substance, which supresses the expression amount of the polypeptide of the present invention, can be carried out among a population of test substances. Otherwise, change of the amount of expression of the RNA having a sequence of the polynucleotide of the present invention caused by a test substance can be also detected quantitatively by a real time PCR method using a short-chain DNA primer including a sequence of the polynucleotide of the present invention. More specifically, the real time PCR can be carried out by the method described in Example 4. Accordingly, screening of a substance which supresses the expression amount of the polypeptide of the present invention can be carried out among a population of test substances. The polynucleotide of the present invention can be used in the method for screening.

<Method of the Production of a Pharmaceutical Composition for Improving Insulin Resistance and/or Improving Glucose Metabolism>

The present present invention involves a method for producing a pharmaceutical composition for improving insulin resistance and/or improving glucose metabolism which comprises carrying out the screening with the method for screening of the present invention, and carrying out the formulation using the substance obtained by the screening.

Formulations containing the substance obtained by the method for screening of the present invention as an active ingredient can be prepared depending on the type of the active ingredient using a carrier, an excipient, and/or other additives, which are usually used for the formulation.

Administration may be, for example, oral administration via a tablet, pill, capsule, granule, subtle granule, powders, or liquid formulation or the like for oral administration, or may be parenteral administration via an injection with e.g., intravenous injection, intramuscular injection or intraarticular injection, a suppository, a transcutaneous administration preparations, or transmucosal administration preparation. In particular, in cases of peptides which are digested in the stomach, parenteral administration such as intravenous injection is preferred.

Solid composition for oral administration may include one or more active substances, and at least one inert diluent admixed therewith such as, for example, lactose, mannitol, glucose, microcrystalline cellulose, hydroxypropyl cellulose, starch, polyvinylpyrrolidone or magnesium aluminometasilicate. The composition may contain additives other than the inert diluent such as, for example, a lubricant, a disintegrant, a stabilizing agent, or a solubilizer or solubilizing agent, according to a known method. Tablets or pills may be coated with a film of such as sugar coating, or gastric or enteric, if necessary.

Liquid compositions for oral administration may include, for example, emulsions, solutions, suspensions, syrups, or elixirs, and may contain a generally used inert diluent, e.g., purified water or ethanol. The composition may contain additives other than the inert diluent such as, for example, a moistening agent, a suspending agent, a sweetners, an aromatic, or antiseptic.

The injections for parenteral administration may include aseptic aqueous or nonaqueous solutions, suspensions, or emulsions. The water soluble solutions or suspensions may include, for example, distilled water for injection, physiological saline or the like as a diluent. As the diluent of water insoluble solutions or suspensions, for example, propyleneglycol, polyethyleneglycol, a vegetable oil (for example, olive oil), an alcohol (for example, ethanol), polysorbate 80 or the like may be included. The composition may further include a moistening agent, an emulsifying agent, a dispersant, a stabilizing agent, a solubilizer or solubilizing agent, or a preservative. The composition can be sterilized by, for example, filtration by passing through a filter for reserving bacteria, mixing with a bacteriocide, or irradiation. In addition, when a sterile solid composition is produced and used, it may be dissolved in sterile water or other sterile medium for injection, and can be used.

The dose may be determined appropriately taking into account of intensity of the activity of the active ingredient, i.e., the substance obtained according to the method for screening of the present invention, symptoms, age of the subject to be administered, or sex.

For example, in case of oral administration, the dose may be usually about 0.1 to 100 mg, and preferably 0.1 to 50 mg per adult (postulating that the body weight is 60 kg) per day. In instances of parenteral administration, the dose may be 0.01 to 50 mg, and preferably 0.01 to 10 mg per day in the dosage form of an injection.

EXAMPLES

Hereinafter, the present invention is explained in detail by Examples, however, the present invention is not limited by those Examples. Unless specifically stated, the present invention can be carried out according to a known method ("Molecular Cloning", Sambrook, J. et al., Cold Spring Harbor Laboratory Press, 1989, and the like). Moreover, when a commercially available reagent or kit is used, it can be carried out according to the protocol attached to the commercial product.

Example 1

Cloning of CAPBP1 Gene and Construction of the Expression Vector (1) Cloning of CAP With reference to a cDNA sequence encoding a full length region of mouse CAP (c-Cbl associated protein) described as Accession No. U58883 of gene database, GenBank, the following four oligo nucleotides named mCAP-5HS, mCAP-1, mCAP-2 and mCAP-3SE were designed as primers (SEQ ID NOs:5 to 8). To mCAP-5HS, a restriction enzyme HindIII site is added, and to mCAP-3SE, a restriction enzyme EcoRI site is added on the 5' side of each primer.

Total RNA was prepared from the skeletal muscle of male 15-weeks old C57BL/6J mice (CLEA Japan, Inc.), and single strand cDNA was produced by reverse transcription to use as a template of PCR for CAP gene cloning. The total RNA was prepared using a reagent for extracting RNA (Isogen: NIPPON GENE CO., LTD.) according to the instruction manual. Thus prepared total RNA was then treated with deoxyribonuclease (NIPPON GENE CO., LTD.), followed by phenol/chloroform treatment and ethanol precipitation. The precipitate was dissolved in sterile water. The reverse transcription from total RNA to single strand cDNAs was carried out with 1 μg of the total RNA using a kit for a reverse transcription reaction (Advantage™, RT-for-PCR Kit; Clontech) in a system of 20 μl.

A gene coding for a N-terminal half of CAP was amplified with a combination of primers of SEQ ID NO:5 and SEQ ID NO:6, and a gene coding for a C-terminal half of CAP was amplified with a combination of primers of SEQ ID NO:7 and SEQ ID NO:8 using PCR, respectively. The PCR was conducted in a reaction system of 50 μl in total volume using 5 μl of the single stranded cDNA, 0.5 μl of Pyrobest DNA Polymerase (Takara Shuzo Co., Ltd.), and each 50 pmol of the primers. The temperature condition for allowing the reaction was: leaving to stand at 95° C. for 3 min, followed by repeating 40 cycles of the step consisting of three steps of 98° C. for 10 sec, 60° C. for 30 sec and 74° C. for 90 sec, and finally 74° C. for 7 min.

Next, the amplified fragment was subcloned into a plasmid pZEr0-2.1 (Invitrogen Corporation) digested with a restriction enzyme EcoRV. Nucleotide sequence of the subcloned gene fragment was determined using a sequencer (ABI 3700 DNA sequencer, Applied Biosystems, Inc.), and confirmed to be identical to the reported nucleotide sequence.

Both of the 3' side of the gene fragment encoding the N-terminal half and the 5' end of the gene fragment encoding the C-terminal half amplified by PCR have a restriction enzyme SacI site which is the only one site endogenously present in the CAP gene. Thus, the gene fragment encoding the N-terminal half could be obtained using restriction enzymes HindIII and SacI, and the gene fragment encoding the C-terminal half could be obtained using restriction enzymes SacI and EcoRI, from the subcloned plasmids, respectively. Full length of the mouse CAP gene could be cloned by simultaneously ligating them with a plasmid pcDNA3.1 (+) (Invitrogen Corporation) digested with restriction enzymes HindIII and EcoRI.

(2) Production of Expression Plasmid for Yeast Two-hybrid

For inserting the mouse CAP cDNA into an expression vector pDBtrp for yeast two-hybrid (Invitrogen Corporation), primers represented by SEQ ID NO:9 and 10 were designed to give a mouse CAP gene sequence to which a homologous region with 40 nucleotides anteroposterion the multicloning site of the pDBtrP vector were added on the 5' side and 3' side, respectively. The PCR was carried out with the mouse CAP plasmid cloned as described above as a template using DNA polymerase (Pyrobest DNA polymerase; Takara Shuzo Co., Ltd.) at 98° C. for 1 min., followed by repeating 35 cycles of 98° C. for 5 sec., 55° C. for 30 sec. and 72° C. for 5 min. Thus resulting DNA fragment has the entire coding region of the mouse CAP gene.

The vector pDBtrp linearlized by digesting with restriction enzymes SalI and NcoI, and the PCR fragment including mouse CAP cDNA obtained as described above were added to a yeast strain MaV203 for two-hybrid (Invitrogen Corporation) at the same time, and transformed with a lithium acetate method (Guthrie C. and Fink R., *Guide to Yeast Genetics and Molecular Biology*, Academic, San Diego, 1991). As a result, homologous recombination was caused within the yeast cells, thereby forming a plasmid of pDBtrP having the mouse CAP cDNA inserted at the multicloning site (hereinafter, abbreviated as pDB-CAP). The yeast cells having the plasmid were selected by culturing on a solid synthetic minimum medium (DIFCO) (20% agarose) lacking tryptophan which is a selection marker of the plasmid. The yeast cells were treated with Zymolyase (Seikagaku Corporation) at room temperature for 30 minutes, followed by the isolation and purification of the plasmid with an alkaline method. Nucleotide sequence of the plasmid was determined using a sequencing kit (Applied Biosystems, Inc.) and a sequencer (ABI 3700 DNA sequencer Applied Biosystems, Inc.), and one having the CAP DNA in which the coding region of the GAL4 DNA binding region of pDEtrp is inserted in conformity with the translation frame thereof was selected.

(3) Yeast Two-hybrid Screening

The yeast strain MaV203 for two-hybrid transformed with the aforementioned pDB-CAP was suspended in 400 ml of a YPD liquid medium (DIFCO), and cultured at 30° C. for about 6 hours until the absorbance at a wavelength of 590 nm becomes from 0.1 to 0.4. Thereafter, the lithium acetate method was carried out to obtain competent cells, and the final quantity of the cells was suspended in 1.0 ml of a 0.1 M lithium-Tris buffer. The cells were transformed with each 20 μg of a human skeletal muscle cDNA library (Clontech, Match Maker cDNA library), and the cells were selected by culturing on a solid synthetic minimum medium (DIFCO) (20% agarose) lacking tryptophan and leucine which are selection markers of the plasmid of pDB-CAP and the library, respectively, to obtain a transformed strain having both plasmids introduced. At the same time, for the same transformed cells, histidine was removed from the medium in addition to tryptophan and leucine in order to select cells in which a reporter gene HIS3 was operated which is expressed when a fusion protein of a GAL4 transcription promoting region binds to a fusion protein of a GAL4 DNA binding region artificially expressed in a two-hybrid system. Furthermore, the transformed cells were cultured on a solid minimum medium (20% agarose) supplemented with 20 mM 3AT (3-amino-1,2,4-triazole; Sigma) which is an inhibitor of the enzyme encoded by HIS3 at 30° C. for 5 days. Under the same conditions, a colony of 3AT resistant yeast showing the expression of a protein which binds to CAP was obtained. After growing these yeast cells on a YPD solid medium for 24 hours, the expression of a lacZ gene which is a reporter indicating binding in the two-hybrid system being different from HIS3 was examined with the β-galactosidase activity as a marker. In connection with the β-galactosidase activity, the yeast cells on the medium were transferred to a nitrocellulose filter, frozen by dipping into liquid nitrogen, and thereafter, thawed at room temperature. The filter was placed on a filter paper which had been soaked in a 0.4% X-GAL (Sigma) solution, and left to stand at 37° C. for 24 hours. Accordingly change of the color into blue due to β-galactosidase was measured. Through selecting the colony including the cell contents transferred on the filter having the color changed from white to blue, yeast cells expressing the protein bound to CAP were specified, and the plasmid derived from the library was extracted from the cells according to the method in *Yeast Protocols Handbook*, Clontech. As a result of determination of nucleotide sequence of the gene fragment included therein using the nucleotide sequence represented by SEQ ID NO:11 (sequence bound to GAL4 AD region; GenBank Accession No. U29899, derived from cloning vector pACT2) as a primer, a sequencing kit (Applied Biosystems, Inc.) and a sequencer (ABI 3700 DNA sequencer, Applied Biosystems, Inc.), it was confirmed that one clone containing the nucleotide sequence represented by SEQ ID NO:1 and two clones containing the nucleotide sequence represented by SEQ ID NO:3 having 9 bases insertion from the 64th position of SEQ ID NO:1 were included.

(4) Cloning of Full Length cDNA of CAPBP1 Gene

As a result of the above paragraph (3), each one plasmid having a gene fragment containing the full length of the nucleotide sequence represented by SEQ ID NO:1 or 3, and a plasmid containing a sequence of following the base of 16th position in the nucleotide sequence represented by SEQ ID NO:1 were obtained from the cDNA library, respectively. Accordingly, presence of a factor which binds to CAP was suggested. Then, a primer having the nucleotide sequence represented by SEQ ID NO:12 corresponding to a complementary chain of a nucleotide sequence of from 525th position to 504th position of the nucleotide sequence represented by SEQ ID NO:1 was synthesized (Proligo LLC), and the amplification of a full length cDNA was attempted with a PCR method from a cDNA library derived from skeletal muscle as described above using the primer and a primer having the nucleotide sequence represented by SEQ ID NO:11. The PCR reaction was carried out using DNA polymerase (TAKARA LA Taq; Takara Shuzo Co., Ltd.) at 94° C. for 3 min, followed by repeating 35 cycles of 94° C. for 30 sec, 58° C. for 1.5 min and 72° C. for 4 min. Then, PCR was further carried out under the same conditions using the PCR product as a template. As a result of separation of the PCR product by agarose gel electrophoresis, amplification of ca. 600 base pairs DNA fragment was confirmed. Thus, the DNA fragment in the reaction liquid was cloned into an expression vector (pcDNA3.1/V5-His-TOPO; Invitrogen Corporation) using TOPO TA Cloning system (Invitrogen Corporation). Nucleotide sequence of the inserted DNA fragment in the resulting plasmid was determined using a primer bound to a T7 promoter region on the vector (TOPO TA Cloning kit/Invitrogen Corporation; SEQ ID NO:13), a sequencing kit (Applied Biosystems, Inc.) and a sequencer (ABI 3700 DNA Sequencer, Applied Biosystems, Inc.). Consequently, a clone containing the DNA sequence represented by SEQ ID NO:1 or 3 was confirmed, and addition of DNA fragment of about 250 base pair further upstream of the 5' side of SEQ ID NO:1 or 3 was found. However, according to a triplet of the DNA encoding the amino acid sequence represented by SEQ ID NO:2 or 4, another initiation codon was not found in upstream of the first ATG (initiation codon) of SEQ ID NOs:1 and 3, and a triplet of the stop codon was present. Accordingly, open reading frame of the gene represented by SEQ ID NOs:1 and 3 were defined. The gene was named as CAPBP1 gene.

(5) Production of CAPBP1 Expression Vector

According to the nucleotide sequence information represented by SEQ ID NOs:1 and 3, CAPBP1 cDNA encoding the net CAPBP1 protein was amplified by a PCR method using SEQ ID NO:14, and SEQ ID NO:12 from a plasmid containing a full length sequence of the CAPBP1 gene obtained in the above paragraph (4). These two kinds of DNA primers have nucleotide sequences which are homologous to a part of the 5' side and 3' side of the CAPBP1 gene represented by SEQ ID NO:1 or 3, respectively. The primer represented by SEQ ID NO:12 was designed such that the stop codon sequence of CAPBP1 was removed in an attempt to allow a V5 epitope derived from the vector (derived from V protein of paramyxovirus SV5, Southern J A (1991) *J. Gen. Virol.*, 72, 1551–1557, 1991) and a His6 tag (Lindner P (1997) *BioTechniques* 22, 140–149) to follow with the same frame as a triplet of the CAPBP1 gene at its 3', after the cloning. The PCR reaction was carried out using DNA polymerase (TAKARA pyrobest; Takara Shuzo Co., Ltd.), at 98° C. for 1 min, followed by repeating 40 cycles of 98° C. for 5 sec, 58° C. for 30 sec and 72° C. for 2 min. Thus resulting DNA fragments containing CAPBP1 cDNAs of 525 base pairs and 534 base pairs, respectively, were cloned into the aforementioned expression vector pcDNA3.1/V5-His-TOPO. Nucleotide sequences of the inserted DNA fragment in thus resulting plasmid were determined in a similar manner to the above paragraph (4). Consequently, it was confirmed that DNAs excluding the 3' side stop codons of the DNA sequences represented by SEQ ID NOs:1 and 3 were inserted, respectively. Hereinafter, the expression plasmid containing the sequence of SEQ ID NO:1 is abbreviated as pcDNA-CAPBP1 (−), and that containing the sequence of SEQ ID NO:3 is abbreviated as pcDNA-CAPBP1 (+3) among these expression plasmids.

Example 2

Production of Culture Cells Expressing CAPBP1 Protein (1) Production of CAPBP1 Expressing Cell The expression plasmid pcDNA-CAPBP1 (−) and pcDNA-CAPBP1 (+3) produced in the above Example 1 (5) were introduced into COS-1 cells, respectively. The COS-1 cells were cultured to be in a 70% confluent state by adding 2 ml of a minimum essential medium DMEM (GIBCO) supplemented with 10% fetal bovine serum (Sigma) to each well on the culture dish of a 6-well culture plate (well diameter of 35 mm). The cells were transiently transfected with pcDNA-CAPBP1 (−) or pcDNA-CAPBP1 (+3) (1.0 μg/well) by a calcium phosphate method (Graham et al., *Virology*, 52, 456, 1973; Naoko Arai, *Gene introduction and expression/Analytical method* (Kaiseki hou) pp. 13–15, 1994). After culturing for 48 hours, the medium was removed, and the cells were washed with a phosphate buffer (hereinafter, abbreviated as PBS). Thereafter, the cells were lysed by adding 0.1 ml of a cell lysis solution (100 mM potassium phosphate (pH 7.8), 0.2% Triton X-100) per well.

(2) Detection of CAPBP1 Protein

To 10 μl of the lysis solution of the CAPBP1 expressing cells in Example 2 (1), a 2-fold concentrated SDS sample buffer (125 mM Tris-HCl (pH 6.8), 3% sodium lauryl sulfate, 20% glycerin, 0.14 M β-mercaptoethanol, 0.02% bromophenol blue) was added, and treated at 100° C. for 2 min. Thereafter, the mixture was loaded on 10% SDS polyacrylamide gel electrophoresis to separate the proteins included in the sample. After transferring the proteins in the polyacrylamide to a nitrocellulose membrane using a semi-dry type blotting apparatus (BioRad), detection of the CAPBP1 protein on the nitrocellulose was carried out by a Western blotting method according to a known procedure. A monoclonal antibody which recognizes a V5 epitope (Invitrogen Corporation) fused to the C-terminus of CAPBP1 was used as a primary antibody, and a rabbit IgG-HRP fusion antibody (BioRad) was used as a secondary antibody. It was confirmed that a protein of about 24 kDa presenting a CAPBP1-V3-His6 fusion protein consisting of 220 or 223 amino acids including the tag of the C-terminal side consisting of 45 amino acids was detected depending on the presence of the expression vector pcDNA-CAPBP1 (−) or pcDNA-CAPBP1 (+3). Accordingly, it was confirmed that the full length region of the aforementioned CAPBP1 gene cloned in the culture cells was certainly expressed and formed a stable structure as a protein.

Example 3

Analysis of Tissue-dependent Distribution of Expression of CAPBP1 Gene

Since the CAPBP1 protein interacts with CAP, it was expected that the protein is expressed in insulin responsive tissues, whereby acting on the insulin signal in the second pathway. Thus, presence or absence of the expression of CAPBP1 in various type of tissues was examined by a PCR reaction from cDNAs derived from the various type of tissues to amplify the full length cDNA fragment of the CAPBP1 gene represented by SEQ ID NO:1 or 3 using a pair of primers which are homologous to CAPBP1 represented by SEQ ID NO:12 and SEQ ID NO:14 as described above. Using DNA polymerase (AmpliTaq$^{(R)}$ DNA polymerase; Applied Biosystems, Inc.) with each in an amount of 1 μg of cDNA libraries derived from human bone marrow, brain, cartilage, heart, kidney, leukocyte, liver, lung, lymphocyte, mammary gland, ovary, pancreas, placenta, prostate gland, skeletal muscle and HeLa cell (Clontech) as a template, PCR cycle of at 98° C. for 5 sec, at 58° C. for 30 sec and at 72° C. for 1.5 min. was repeated 35 times after the treatment of at 98° C. for 1 min. As a result of separation of thus obtained PCR product by agarose gel electrophoresis, a DNA fragment of about 500 base pairs which is considered to include a desired partial fragment of CAPBP1 was amplified from each cDNA library derived from skeletal muscle, HeLa cell, brain, lymphocyte and mammary gland. After separating each of these DNA fragments from the agarose gel, nucleotide sequence of the DNA fragment was determined respectively using a primer represented by SEQ ID NO:14 according to the method described in the above Example 1 (4). Consequently, it was confirmed that they have a sequence which is identical to CAPBP1 represented by SEQ ID NO:1 or 3. Therefore, expression of the present CAPBP1 gene represented by SEQ ID NO:1 and SEQ ID NO:3 was revealed to be controlled specifically in limited organs including skeletal muscle which is responsive to the insulin signal.

Example 4

Measurement of Amount of Expression of CAPBP1 in Normal and Diabetic Model Mice

From the findings described above, the CAPBP1 protein of the present invention was revealed to bind to CAP, and to be expressed in insulin responsive tissues such as skeletal muscle. Since the CAP protein is a factor which acts on the insulin signal in the second pathway, involvement of the mode of operation of CAPBP1 of the present invention in insulin resistance was expected. Therefore, amounts of expression of messenger RNAs (mRNAs) of the CAPBP1 gene in skeletal muscle of two kinds of diabetic model mice KKA$^y$/Ta (Iwatsuka et al., *Endocrinol. Japon.*, 17, 23–35, 1970, Taketomi et al., *Horm. Metab. Res.*, 7, 242–246, 1975), and C57BL/KsJ-db/db (Chen. et al., *Cell*, 84, 491–495, 1996; Lee et al., *Nature*, 379, 632–635, 1996; Kaku et al., *Diabetologia*, 32, 636–643, 1989) were measured, and compared.

With regard to the expression amount of the gene, the amount of expression of the mouse orthologue of CAPBP1 gene of the present invention was measured, and corrected based on the expression amount of simultaneously measured glyceraldehyde 3-phosphate dehydrogenase (G3PDH) gene. As the measurement system, PRISM™ 7700 Sequence Detection System and SYBR Green PCR Master Mix (Applied Biosystems, Inc.) were used. In this measurement system, expression amount of the intended gene was determined through detecting and quantitatively identifying the amount of fluorescence of the SYBR Green 1 dye incorporated by the double strand DNA amplified by PCR.

Specifically, the measurement was conducted according to the following procedure.

(1) Preparation of Total RNA

Total RNA was prepared from skeletal muscle of 15-weeks old male C57BL/6J mice, KKA$^y$/Ta mice, C57BL/KsJ-dbm m+/m+ mice, C57BL/KsJ-dbm db/db mice (all of which from CLEA Japan, Inc.) using an RNA extraction reagent (Isogen; NIPPON GENE CO., LTD.) according to the instruction manual. It is known that the C57BL/6J mice and C57BL/KsJ-dbm m+/m+ mice are healthy mouse, while KKA$^y$/Ta mice and C57BL/KsJ-dbm db/db mice are known as type 2 diabetic model mice. The prepared total RNA was thereafter treated with deoxyribonuclease (NIPPON GENE CO., LTD.), treated with phenol/chloroform, precipitated with ethanol, dissolved in sterile water, and stored at −20° C.

(2) Synthesis of a Single Strand cDNA

Reverse transcription from the total RNA into single strand cDNA was carried out using 0.25 μg of RNA, in the system of 20 μl using a kit for reverse transcription reaction (Advantage™ RT-for-PCR Kit; Clontech). After the reverse transcription, 180 μl of sterile water were added and stored at −20° C.

(3) Production of PCR Primer

The following 4 oligonucleotides named as CAP1403, CAP1404, G3PDH F and G3PDH R (SEQ ID NOs:15 to 18) were designed as PCR primers described in paragraph (4). Combination of SEQ ID NO:15 and SEQ ID NO:16 was used for the CAPBP1 gene, while combination of SEQ ID NO:17 and SEQ ID NO:18 was used for the G3PDH gene.

(4) Measurement of Amount of Gene Expression

Real time measurement of PCR amplification by PRISM™ 7700 Sequence Detection System was carried out in a 25 μl system according to the instruction manual. In each system, 5 μl of the single strand cDNA, 12.5 μl of 2×SYBR Green reagent, and 7.5 pmol of each primer were used. In addition, for the preparation of a calibration curve, 5 μl of properly diluted 0.1 μg/μl mouse genomic DNA (Clontech) which was used in place of the single strand cDNA. The PCR was carried out at 50° C. for 10 min, and then at 95° C. for 10 min, followed by repeating 45 cycles of two steps of 95° C. for 15 sec and 60° C. for 60 sec.

Figure 1:
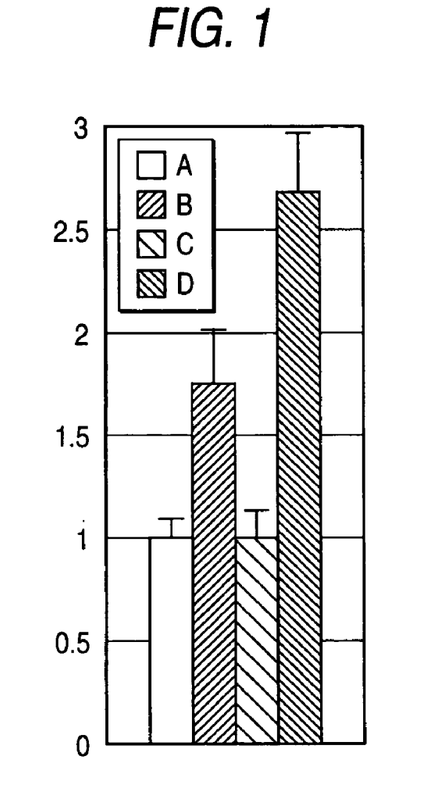
FIG. 1 is a drawing showing the comparison of expression level of CAPBP1 in muscle tissues in diabetic model mice KKA[y] and db/db, and normal mice. The vertical axis indicates relative expression level in mice muscle. Results are shown from the sample of C57BL/6J mice by bar A, KKA[y]/Ta mice by bar B, C57BL/KsJ-dbm m+/m+ mice by bar C, and C57BL/KsJ-dbm db/db mice by bar D.

The expression amount of mouse CAPBP1 gene in each sample was corrected with the amount of G3PDH expression on the basis of the following formula:

[corrected expression amount of CAPBP1]=
[CAPBP1 gene expression amount (raw data)]/
[G3PDH gene expression amount (raw data)].

As a result, as shown in FIG. 1, it was revealed that expression of the mouse orthologue gene of the CAPBP1 of the present invention is markedly increased in skeletal muscle of the diabetic model mice. Therefore, the CAPBP1 of the present invention is believed to induce the insulin resistance through the hyperfunction in muscle. From the foregoings, it is concluded that the CAPBP1 of the present invention greatly participates in insulin resistance.

Also, it was found from the results of the Example that measurement of the amount of CAPBP1 expression enables diagnoses of diabetic pathologic conditions.

Example 5

Verification of Interaction of CAPBP1 and CAP (1) Recloning of CAP Gene

Using the cDNA sequence encoding the mouse CAP full length region cloned in the above Example 1 as a template, and oligonucleotides represented by SEQ ID NO:19 and SEQ ID NO:20 designed such that a FLAG sequence is added to C-terminus as a primer, PCR was carried out using DNA polymerase (Pyrobest DNA Polymerase (Takara Shuzo Co., Ltd.)), under a condition of a thermal denaturation reaction at 95° C. for 3 minutes followed by 40 cycles of 98° C. for 10 sec, 60° C. for 30 sec, and 74° C. for 1 min and 30 sec, and additionally 74° C. for 7 min. Thus produced DNA fragment of about 2.5 kbp was cloned into a plasmid pcDNA3.1/V5-His-TOPO (Invitrogen Corporation). Thus resulting plasmid was named as pcDNA-CAP-FLAG. Nucleotide sequence of the CAP cDNA cloned on the vector was determined using the oligonucleotide represented by SEQ ID NO:13 described above as a primer, a sequencing kit (Applied Biosystems, Inc.) and a sequencer (ABI 3700 DNA sequencer, Applied Biosystems, Inc.), and confirmed to be identical with the reported sequence.

(2) Production of GST-Fused CAPBP1 Expression Plasmid

In order to insert a human CAPBP1 cDNA into a GST fusion expression vector pGEX-6P-1 (Amersham Biosciences K.K.), the pcDNA-CAPBP1 (−) obtained as described above was treated with enzymes BamHI and XhoI to prepare a CAPBP1 cDNA fragment. Moreover, using linker oligos which form EcoRI and BamHI fragments at both ends (SEQ ID NOs:21 and 22), recombination was carried out at EcoRI and XhoI site of pGEX-6P-1 to obtain pGEX-CAPBP1.

(3) Purification of GST-Fused CAPBP1 Protein

Transformation of the plasmid pGEX-CAPBP1 obtained in the above paragraph (2) was carried out using *Escherichia coli* BL21 with a heat shock method, and culture with shaking was carried out in 2.4 mL of culture overnight. Thereafter, the entire volume was transferred to 400 mL of culture, followed by culture with shaking at 37° C. for 3 hours. Then, IPTG (Sigma) was added thereto to give a final concentration of 2.5 mM, followed by additional shaking culture for 3 hours to induce the expression of a GST-fused CAPBP1 protein (hereinafter, abbreviated as GST-CAPBP1). The bacterial bodies were recovered, and GST-CAPBP1 was purified on glutathione Sepharose beads (Glutathione Sepharose 4B; Amersham Pharmacia) according to a known procedure (Experimental engineering, Vol. 13, No. 6. 1994, p. 528, Matsushime et al.). As a control, a protein including the GST part alone (hereinafter, abbreviated as GST protein) was induced to be expressed and purified similarly to the manner as described above from *Escherichia coli* BL21 transformed with pGEX-6P-1. These purified proteins were subjected to separation by SDS gel electrophoresis and staining with Coomassie Brilliant Blue according to known methods, and thus, it was confirmed that the proteins have the expected molecular weight (GST-CAPBP1; 50 kDa, GST protein; 26 kDa) were purified.

(4) Confirmation of Biochemical Binding Between CAP Protein and CAPBP1 Protein

Using the GST-fused CAPBP1 protein (GST-CAPBP1) produced in the above paragraph (3), presence or absence of direct interaction between the CAPBP1 protein and the CAP protein was confirmed by a GST-pulldown method (*Experimental engineering*, Vol. 13, No. 6. 1994, p. 528, Matsushime et al.).

First, gene introduction of 15 μg of the pcDNA-CAP-FLAG produced in the paragraph (1) into 293T cells cultured in a 10 cm-dish was conducted using lipofectamine 2000. As a negative control, similar operation was carried out without any plasmid. After 48 hours following the gene introduction, cells were lysed in 1 mL of a cell lysis solution (50 mM Tris-HCl (pH 7.5), 10% glycerol, 120 mM NaCl, 1 mM EDTA, 0.1 mM EGTA, 0.5 mM PMSF, 0.5% NP-40). Each 300 μl of this cell lysate and each 30 μg of the GST protein or GST-CAPBP1 purified on the glutathione beads as in the above paragraph (3) were mixed, and shaken at 4° C. for 1 hour. Thereafter, the protein which bound to the GST protein or GST-CAPBP1 on the beads was coprecipitated by centrifugation. This precipitate was suspended in 0.5 ml of a buffer prepared by changing the NaCl concentration of the cell lysis liquid into 100 mM, and then coprecipitated again by centrifugation. After repeating these operations four times, the protein in the precipitate was separated by SDS gel electrophoresis according to a known procedure, and analyzed by a Western blotting method using an anti-FLAG antibody (Sigma). As a result, a band having a size supposed to correspond to CAP-FLAG was detected by the anti-FLAG antibody only in case where the lysate of pcDNA-CAP-FLAG introduced cell and the GST-CAPBP1 were mixed. This suggests that CAP bound to CAPBP1 to result in coprecipitation. As described above, the CAPBP1 of the present invention was revealed to interact with the CAP protein. Therefore, the CAPBP1 of the present invention is believed to participate in inducing insulin resistance via the interaction with a CAP protein.

Example 6

Measurement of Glucose Uptake Activity in Cells which Highly Express CAPBP1

(1) Production of Viruses which Highly Express CAPBP1 Using an Adenovirus Vector A gene fragment encoding for human CAPBP1 was obtained using restriction enzymes of BamHI and PstI from a pcDNA-CAPBP1 (−) vector, and furthermore, inserted into a multicloning site (BamHI and NotI) of an adenoviral vector pAdTrack-CMV (obtained from Cancer Center at Johns Hopkins) using linger oligos which form PstI and NotI cleavage fragments at both ends and which contain a FLAG sequence (SEQ ID NOs:23 and 24). Accordingly, a CAPBP1/pAdTrack-CMV vector was obtained.

Hereinafter, according to a known protocol ("A Practical Guide for using the AdEasy system", HYPERLINK www-.coloncancer.org/adeasy.htm, "www.coloncancer.org/adeasy/protocol2.htm"), preparation of an adenoviral liquid having high titer to express CAPBP1 was carried out. Adenovirus for use as a control was prepared from pAdTrack-CMV.

With respect to the amount of the virus, absorbance at 260 nm (A260) was measured, and converted according to the following formula:

$$A260=1.1\times10^{12} \text{ viral particles}=3.3\times 10^{11} \text{ pfu/ml.} \quad \text{[formula]1}$$

(2) Differentiation of Adipocytes and Addition of CAPBP1 Expressing Adenovirus

Effect of CAPBP1 on sugar incorporation was evaluated using 3T3-L1 cells. 3T3-L1 cells were suspended in Dulbecco's modified Eagle medium (DMEM) containing 10% fetal calf serum (FCS), and dispensed into a collagen-coated 24-well plate (ASAHI TECHNO GLASS CORPORATION) to give $1.6\times10^5$ cells/well. Next day, the medium was changed into DMEM (10% FCS) supplemented with 10 μg/ml insulin, 250 nM dexamethasone and 0.5 mM 3-isobutyl-1-methylxanthine (IBMX) to induce differentiation of the 3T3-L1 cells. Two days later, the medium was replaced to 0.4 ml of DMEM (10% FCS) again. Four days thereafter, adenovirus to allow CAPBP1 to be expressed was added to the medium at a density of $1.6\times10^{10}$ pfu per well. As a control, adenovirus to allow eGFP alone to be expressed was used.

(3) Measurement of Glucose Uptake Activity in Cells which Highly Express CAPBP1

Figure 2:
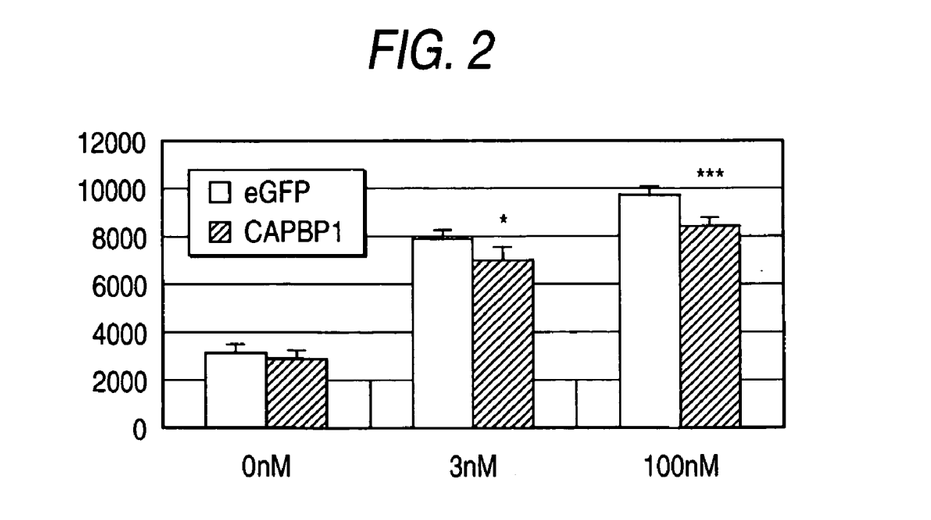
FIG. 2 is a drawing illustrating the inhibition of glucose uptake activity in adipocytes in which CAPBP1 is overexpressed. The vertical axis in the Figure indicates the amount of incorporation (cpm) of 2-deoxy-glucose, and the horizontal axis indicates the insulin concentration.

After 36 hours of the addition of adenovirus, the medium was changed into DMEM without fetal calf serum, and left to stand for 3 hours. Then, the effect on sugar incorporation was evaluated. First, the medium was changed into 0.25 ml of KRP buffer (136 mM NaCl, 4.7 mM KCl, 1.25 mM $CaCl_2$, 1.25 mM $MgSO_4$, 5 mM $Na_2HPO_4$, pH 7.4) containing insulin at a predetermined concentration, and incubated at 37° C. for 20 min. Next, KRP containing 1 mM 2-deoxy-D-glucose supplemented with 15 μl of 2-deoxy-D-[U-$^{14}$C] glucose (Amersham Biosciences K.K.) per ml was provided and each 50 μl of which was added to each well, and incubated at 37° C. for 10 min. Thereafter, the cells were washed with ice-cooled phosphate buffered physiological saline (PBS) three times, and lysed with 0.1% sodium lauryl sulfate (SDS). After mixing with 2 ml of a scintillator (Aquazol-2, Packard BioScience Company Inc.), amount of glucose incorporated into the cells was measured using a liquid scintillation analyzer (Tri-Carb B2500TR, Packard). As shown in FIG. 2, expression of CAPBP1 significantly lowered the amount of glucose which was incorporated into the cells. Thus, it was shown that the CAPBP1 of the present invention acts as an exacerbating factor of diabetic conditions by way of its overexpression through preventing the incorporation of sugar into the cells. For reference, the symbol "*" in the Figure represents the evaluation in Student's t-test. "*" means that significant difference from the control group is p<0.05, while "***" means that the significant difference is p<0.001.

Example 7

Detection of Interaction between CAPBP1 and GSK-3α

From the results described above, it was revealed that CAPBP1 inhibits the incorporation of sugar into cells through binding to CAP downstream of the insulin signal. If CAPBP1 is involved in glucose metabolism in cells, it is expected to act also on glucose metabolism-related proteins other than CAP. Therefore, as a result of examination of interactions of multiple glucose metabolism-related proteins with CAPBP1, it was newly found that the protein binds to a GSK-3α protein having an activity to inactivate glycogen synthase through phosphorylation.

(1) Cloning of GSK-3α Gene

Full length cDNA of GSK3α was obtained with the sequence information of human GSK3α of GenBank Accession No. NM_019884, from a human smooth muscle cDNA library (Clontech) using DNA oligoprimers represented by SEQ ID NO:25 and SEQ ID NO:26 (Proligo LLC) according to the identical PCR and cloning methods with those demonstrated in the above Example 1 (4), and cloned into an expression vector (pcDNA3.1/V5-His-TOPO; Invitrogen Corporation). Upon this procedure, the design was executed such that a FLAG tag was inserted into N-terminal side of GSK3α. The expression plasmid was named as pcDNA3.1-FLAG-GSK3α.

(2) Detection of Biochemical Binding Between CAPBP1 and GSK3α

Both pcDNA-CAPBP1 (−) produced in the above Example 1 (5) and the aforementioned pcDNA3.1-FLAG-GSK3α were cotransfected into COS-1 cells according to the method described in above Example 2 (1), and cultured for 48 hours. After recovering the cells, the protein bound to GSK3α was separated using an anti-FLAG antibody (Sigma) according to a known immunoprecipitation procedure (Experimental Medicine (Jikken Igaku) supplementary volume, Biomanual series 7, YODOSHA CO., LTD., 1994, p. 91, Michinari Hamaguchi). Presence of the CAPBP1-V3-His6 fusion protein was examined in the separated protein by SDS polyacrylamide electrophoresis and a Western blotting method in which an anti-V5 antibody (Invitrogen Corporation) was used. Consequently, a band of 24 kDa of the CAPBP1-V3-His6 fusion protein was detected only from the cellular fraction in which the protein and FLAG-GSK3α were simultaneously expressed. Accordingly, the binding between both proteins was shown.

GSK-3 inactivates glycogen synthase through phosphorylation, to suppress incorporation of sugar into cells. Also, GSK-3α is phosphorylated by PKB which is activated by insulin signal, and thus, its activity is suppressed. From these facts, the protein is considered to be a molecule which negatively acts on the insulin signal (*Biochem J.*, 1993, 294 (3): pp. 625–629). From the fact of binding to GSK3α, the CAPBP1 of the present invention was found to participate in inducing diabetic conditions through negatively controlling the insulin signal.

INDUSTRIAL APPLICABILITY

CAPBP1 is a novel molecule involved in insulin signal, and thus, the polypeptide polynucleotide, expression vector and cell of the present invention can be used for identification and screening of an agent for improving insulin resistance and/or an agent for improving diabetes. Moreover, the polynucleotide of the present invention exhibiting the increased expression amount in a diabetic condition is useful in diagnosis of diabetes.

Sequence Listing Free Text

Reference number <223> in Sequence Listing below is for describing explanation of "Artificial Sequence". Specifically, each nucleotide sequence represented by SEQ ID NOs:5 to 10, 12 to 18, 23 and 24 in the Sequence Listing is an artificially synthesized primer sequence. The nucleotide sequence represented by the sequence of SEQ ID NO:11 is a sequence consisting of bases of from the 5183rd position (5') to 5162nd position (3') of a cloning vector pACT2 (GenBank U29899).

In the foregoings, the present invention was explained with reference to particular embodiments, however, alterations and modifications obvious to persons skilled in the art are involved in the scope of the present invention.

---

The invention claimed is:

1. An isolated polypeptide which comprises the amino acid sequence represented by SEQ ID NO:2 or 4, and binds to c-Cbl-associated protein (CAP); or an isolated polypeptide which consists of the amino acid sequence in which 1 to 3 amino acids are deleted, substituted, and/or inserted in the amino acid sequence represented by SEQ ID NO:2 or 4, and binds to CAP.

2. An isolated polypeptide which consists of an amino acid sequence having a sequence identity of 98% or more with the amino acid sequence represented by SEQ ID NO:2 or 4, and is a protein which binds to CAP.

3. An isolated polypeptide consisting of the amino acid sequence represented by SEQ ID NO:2 or 4.

4. A method of screening for an inhibitor of the binding between CAP and the polypeptide according to any one of claims 1 to 3 comprising:

measuring the binding between CAP and said polypeptide in both the presence and absence of a test substance, wherein a decrease in the binding between CAP and said polypeptide in the presence of the test substance compared to its absence indicates inhibition.

5. The isolated polypeptide according to claim 1, which comprises the amino acid sequence represented by SEQ ID NO:2 or 4, and binds to c-Cbl-associated protein.

* * * * *

SEQUENCE LISTING

<160> NUMBER OF SEQ ID NOS: 26

<210> SEQ ID NO 1
<211> LENGTH: 528
<212> TYPE: DNA
<213> ORGANISM: Homo sapiens
<220> FEATURE:
<221> NAME/KEY: CDS
<222> LOCATION: (1)..(525)

<400> SEQUENCE: 1

```
atg cgg cga tcg agg agc tct gcg gcc gcc aag ctg cgc ggg cag aag      48
Met Arg Arg Ser Arg Ser Ser Ala Ala Ala Lys Leu Arg Gly Gln Lys
1               5                   10                  15 cgg tcc ggg gcc tcc gcg gcc ccc gcg gcc tcc gcg gcc gct gcc ttg      96
Arg Ser Gly Ala Ser Ala Ala Pro Ala Ala Ser Ala Ala Ala Ala Leu
                20                  25                  30 gca ccc agc gcc acc cgc aca cgg cgc tcc gct agc cag gcc ggg agc     144
Ala Pro Ser Ala Thr Arg Thr Arg Arg Ser Ala Ser Gln Ala Gly Ser
            35                  40                  45 aag agc cag gcg gtg gag aag ccg ccg tcg gag aag ccg cgg ctg agg     192
Lys Ser Gln Ala Val Glu Lys Pro Pro Ser Glu Lys Pro Arg Leu Arg
        50                  55                  60 cgc tcg tcg ccg cgg gcc cag gag gag ggc ccg ggg gag ccg ccg ccg     240
Arg Ser Ser Pro Arg Ala Gln Glu Glu Gly Pro Gly Glu Pro Pro Pro
65                  70                  75                  80 cct gag ctg gcg ttg ctc ccg cca ccg ccg ccg ccg ccg act ccc         288
Pro Glu Leu Ala Leu Leu Pro Pro Pro Pro Pro Pro Pro Thr Pro
                85                  90                  95 gcg acc ccg acg tcc tcg gcg tcc aac ctg gac ctg ggc gag cag cgg     336
Ala Thr Pro Thr Ser Ser Ala Ser Asn Leu Asp Leu Gly Glu Gln Arg
                100                 105                 110 gag cgc tgg gag acg ttc cag aag cgg cag aag ctt acc tcc gag ggt     384
Glu Arg Trp Glu Thr Phe Gln Lys Arg Gln Lys Leu Thr Ser Glu Gly
            115                 120                 125 gcc gcc aag ctc ctg cta gac acc ttt gaa tac cag ggc ctg gtg aag     432
Ala Ala Lys Leu Leu Leu Asp Thr Phe Glu Tyr Gln Gly Leu Val Lys
        130                 135                 140 cac aca gga ggc tgc cac tgt gga gca gtt cgt ttt gaa gtt tgg gcc     480
His Thr Gly Gly Cys His Cys Gly Ala Val Arg Phe Glu Val Trp Ala
145                 150                 155                 160 tca gca gac ttg cat ata ttt gac tgc aag tac cgg aat tat ata tga     528
Ser Ala Asp Leu His Ile Phe Asp Cys Lys Tyr Arg Asn Tyr Ile
                165                 170                 175
```

<210> SEQ ID NO 2
<211> LENGTH: 175
<212> TYPE: PRT
<213> ORGANISM: Homo sapiens

<400> SEQUENCE: 2

```
Met Arg Arg Ser Arg Ser Ser Ala Ala Ala Lys Leu Arg Gly Gln Lys
1               5                   10                  15

Arg Ser Gly Ala Ser Ala Ala Pro Ala Ala Ser Ala Ala Ala Ala Leu
                20                  25                  30
```

```
Ala Pro Ser Ala Thr Arg Thr Arg Arg Ser Ala Ser Gln Ala Gly Ser
         35                  40                  45

Lys Ser Gln Ala Val Glu Lys Pro Pro Ser Glu Lys Pro Arg Leu Arg
 50                  55                  60

Arg Ser Ser Pro Arg Ala Gln Glu Glu Gly Pro Gly Glu Pro Pro
 65                  70                  75                  80

Pro Glu Leu Ala Leu Leu Pro Pro Pro Pro Pro Pro Thr Pro
                 85                  90                  95

Ala Thr Pro Thr Ser Ser Ala Ser Asn Leu Asp Leu Gly Glu Gln Arg
             100                 105                 110

Glu Arg Trp Glu Thr Phe Gln Lys Arg Gln Lys Leu Thr Ser Glu Gly
             115                 120                 125

Ala Ala Lys Leu Leu Leu Asp Thr Phe Glu Tyr Gln Gly Leu Val Lys
130                 135                 140

His Thr Gly Gly Cys His Cys Gly Ala Val Arg Phe Glu Val Trp Ala
145                 150                 155                 160

Ser Ala Asp Leu His Ile Phe Asp Cys Lys Tyr Arg Asn Tyr Ile
                165                 170                 175

<210> SEQ ID NO 3
<211> LENGTH: 537
<212> TYPE: DNA
<213> ORGANISM: Homo sapiens
<220> FEATURE:
<221> NAME/KEY: CDS
<222> LOCATION: (1)..(534)

<400> SEQUENCE: 3
```

| | | | | | | | | | | | | | | | | |
|---|---|---|---|---|---|---|---|---|---|---|---|---|---|---|---|---|
| atg | cgg | cga | tcg | agg | agc | tct | gcg | gcc | gcc | aag | ctg | cgc | ggg | cag | aag | 48 |
| Met | Arg | Arg | Ser | Arg | Ser | Ser | Ala | Ala | Ala | Lys | Leu | Arg | Gly | Gln | Lys | |
| 1 | | | | 5 | | | | | 10 | | | | | 15 | | |
| cgg | tcc | ggg | gcc | tcc | ggg | gcc | tcc | gcg | gcc | ccc | gcg | gcc | tcc | gcg | gcc | 96 |
| Arg | Ser | Gly | Ala | Ser | Gly | Ala | Ser | Ala | Ala | Pro | Ala | Ala | Ser | Ala | Ala | |
| | | | 20 | | | | 25 | | | | | 30 | | | | |
| gct | gcc | ttg | gca | ccc | agc | gcc | acc | cgc | aca | cgg | cgc | tcc | gct | agc | cag | 144 |
| Ala | Ala | Leu | Ala | Pro | Ser | Ala | Thr | Arg | Thr | Arg | Arg | Ser | Ala | Ser | Gln | |
| | 35 | | | | | 40 | | | | | 45 | | | | | |
| gcc | ggg | agc | aag | agc | cag | gcg | gtg | gag | aag | ccg | ccg | tcg | gag | aag | ccg | 192 |
| Ala | Gly | Ser | Lys | Ser | Gln | Ala | Val | Glu | Lys | Pro | Pro | Ser | Glu | Lys | Pro | |
| 50 | | | | | 55 | | | | | 60 | | | | | | |
| cgg | ctg | agg | cgc | tcg | tcg | ccg | cgg | gcc | cag | gag | gag | ggc | ccg | ggg | gag | 240 |
| Arg | Leu | Arg | Arg | Ser | Ser | Pro | Arg | Ala | Gln | Glu | Glu | Gly | Pro | Gly | Glu | |
| 65 | | | | | 70 | | | | | 75 | | | | | 80 | |
| ccg | ccg | ccg | cct | gag | ctg | gcg | ttg | ctc | ccg | cca | ccg | ccg | ccg | ccg | | 288 |
| Pro | Pro | Pro | Pro | Glu | Leu | Ala | Leu | Leu | Pro | Pro | Pro | Pro | Pro | Pro | | |
| | | | | 85 | | | | | 90 | | | | | 95 | | |
| ccg | act | ccc | gcg | acc | ccg | acg | tcc | tcg | gcg | tcc | aac | ctg | gac | ctg | ggc | 336 |
| Pro | Thr | Pro | Ala | Thr | Pro | Thr | Ser | Ser | Ala | Ser | Asn | Leu | Asp | Leu | Gly | |
| | | | 100 | | | | 105 | | | | | 110 | | | | |
| gag | cag | cgg | gag | cgc | tgg | gag | acg | ttc | cag | aag | cgg | cag | aag | ctt | acc | 384 |
| Glu | Gln | Arg | Glu | Arg | Trp | Glu | Thr | Phe | Gln | Lys | Arg | Gln | Lys | Leu | Thr | |
| | | 115 | | | | | 120 | | | | | 125 | | | | |
| tcc | gag | ggt | gcc | gcc | aag | ctc | ctg | cta | gac | acc | ttt | gaa | tac | cag | ggc | 432 |
| Ser | Glu | Gly | Ala | Ala | Lys | Leu | Leu | Leu | Asp | Thr | Phe | Glu | Tyr | Gln | Gly | |
| 130 | | | | | 135 | | | | | 140 | | | | | | |
| ctg | gtg | aag | cac | aca | gga | ggc | tgc | cac | tgt | gga | gca | gtt | cgt | ttt | gaa | 480 |
| Leu | Val | Lys | His | Thr | Gly | Gly | Cys | His | Cys | Gly | Ala | Val | Arg | Phe | Glu | |
| 145 | | | | | 150 | | | | | 155 | | | | | 160 | |
| gtt | tgg | gcc | tca | gca | gac | ttg | cat | ata | ttt | gac | tgc | aag | tac | cgg | aat | 528 |

```
Val Trp Ala Ser Ala Asp Leu His Ile Phe Asp Cys Lys Tyr Arg Asn
            165                 170                 175 tat ata tga                                                              537
Tyr Ile <210> SEQ ID NO 4
<211> LENGTH: 178
<212> TYPE: PRT
<213> ORGANISM: Homo sapiens

<400> SEQUENCE: 4

Met Arg Arg Ser Arg Ser Ser Ala Ala Lys Leu Arg Gly Gln Lys
  1               5                  10                  15

Arg Ser Gly Ala Ser Gly Ala Ser Ala Ala Pro Ala Ala Ser Ala Ala
             20                  25                  30

Ala Leu Ala Pro Ser Ala Thr Arg Thr Arg Arg Ser Ala Ser Gln
         35                  40                  45

Ala Gly Ser Lys Ser Gln Ala Val Glu Lys Pro Ser Glu Lys Pro
     50                  55                  60

Arg Leu Arg Arg Ser Ser Pro Arg Ala Gln Glu Glu Gly Pro Gly Glu
 65                  70                  75                  80

Pro Pro Pro Pro Glu Leu Ala Leu Leu Pro Pro Pro Pro Pro
                 85                  90                  95

Pro Thr Pro Ala Thr Pro Thr Ser Ser Ala Ser Asn Leu Asp Leu Gly
            100                 105                 110

Glu Gln Arg Glu Arg Trp Glu Thr Phe Gln Lys Arg Gln Lys Leu Thr
            115                 120                 125

Ser Glu Gly Ala Ala Lys Leu Leu Leu Asp Thr Phe Glu Tyr Gln Gly
        130                 135                 140

Leu Val Lys His Thr Gly Gly Cys His Cys Gly Ala Val Arg Phe Glu
145                 150                 155                 160

Val Trp Ala Ser Ala Asp Leu His Ile Phe Asp Cys Lys Tyr Arg Asn
            165                 170                 175

Tyr Ile

<210> SEQ ID NO 5
<211> LENGTH: 45
<212> TYPE: DNA
<213> ORGANISM: Artificial Sequence
<220> FEATURE:
<223> OTHER INFORMATION: Primer Sequence

<400> SEQUENCE: 5
gcaagcttgt cgaccatgag ttctgaatgt gatgttggaa gctct                           45

<210> SEQ ID NO 6
<211> LENGTH: 30
<212> TYPE: DNA
<213> ORGANISM: Artificial Sequence
<220> FEATURE:
<223> OTHER INFORMATION: Primer Sequence

<400> SEQUENCE: 6
ctgacgtaat gtctggagtc gggctgactg                                            30

<210> SEQ ID NO 7
<211> LENGTH: 30
<212> TYPE: DNA
<213> ORGANISM: Artificial Sequence
<220> FEATURE:
```

<223> OTHER INFORMATION: Primer Sequence

<400> SEQUENCE: 7
agccgggcaa gtcttcggtc ctgaccaatg                30

<210> SEQ ID NO 8
<211> LENGTH: 44
<212> TYPE: DNA
<213> ORGANISM: Artificial Sequence
<220> FEATURE:
<223> OTHER INFORMATION: Primer Sequence

<400> SEQUENCE: 8
cggaattcgt cgactgcttt ttagtcttct tatagatata aagg                44

<210> SEQ ID NO 9
<211> LENGTH: 62
<212> TYPE: DNA
<213> ORGANISM: Artificial Sequence
<220> FEATURE:
<223> OTHER INFORMATION: Primer Sequence

<400> SEQUENCE: 9
agagagtagt aacaaaggtc aaagacagtt gactgtatcg atgagttctg aatgtgatgt                60
tg                62

<210> SEQ ID NO 10
<211> LENGTH: 64
<212> TYPE: DNA
<213> ORGANISM: Artificial Sequence
<220> FEATURE:
<223> OTHER INFORMATION: Primer Sequence

<400> SEQUENCE: 10
tggagacttg accaaacctc tggcgaagaa gtccaaagct tatagatata aaggttttac                60
atag                64

<210> SEQ ID NO 11
<211> LENGTH: 22
<212> TYPE: DNA
<213> ORGANISM: Artificial Sequence
<220> FEATURE:
<223> OTHER INFORMATION: Primer Sequence

<400> SEQUENCE: 11 cgcgttttgga atcactacag gg                22

<210> SEQ ID NO 12
<211> LENGTH: 22
<212> TYPE: DNA
<213> ORGANISM: Artificial Sequence
<220> FEATURE:
<223> OTHER INFORMATION: Primer Sequence

<400> SEQUENCE: 12
tatataattc cggtacttgc ag                22

<210> SEQ ID NO 13
<211> LENGTH: 20
<212> TYPE: DNA
<213> ORGANISM: Artificial Sequence
<220> FEATURE:
<223> OTHER INFORMATION: Primer Sequence

<400> SEQUENCE: 13

```
taatacgact cactataggg                                              20

<210> SEQ ID NO 14
<211> LENGTH: 18
<212> TYPE: DNA
<213> ORGANISM: Artificial Sequence
<220> FEATURE:
<223> OTHER INFORMATION: Primer Sequence

<400> SEQUENCE: 14
atgcggcgat cgaggagc                                                18

<210> SEQ ID NO 15
<211> LENGTH: 21
<212> TYPE: DNA
<213> ORGANISM: Artificial Sequence
<220> FEATURE:
<223> OTHER INFORMATION: Primer Sequence

<400> SEQUENCE: 15
gacctggggg agcagcggga g                                            21

<210> SEQ ID NO 16
<211> LENGTH: 20
<212> TYPE: DNA
<213> ORGANISM: Artificial Sequence
<220> FEATURE:
<223> OTHER INFORMATION: Primer Sequence

<400> SEQUENCE: 16
ggtgtccagc agcagcttgg                                              20

<210> SEQ ID NO 17
<211> LENGTH: 20
<212> TYPE: DNA
<213> ORGANISM: Artificial Sequence
<220> FEATURE:
<223> OTHER INFORMATION: Primer Sequence

<400> SEQUENCE: 17
aaagtggaga ttgttgccat                                              20

<210> SEQ ID NO 18
<211> LENGTH: 19
<212> TYPE: DNA
<213> ORGANISM: Artificial Sequence
<220> FEATURE:
<223> OTHER INFORMATION: Primer Sequence

<400> SEQUENCE: 18
ttgactgtgc cgttgaatt                                               19

<210> SEQ ID NO 19
<211> LENGTH: 21
<212> TYPE: DNA
<213> ORGANISM: Mus sp.

<400> SEQUENCE: 19
atgagttctg aatgtgatgt t                                            21

<210> SEQ ID NO 20
<211> LENGTH: 52
<212> TYPE: DNA
<213> ORGANISM: Mus sp.
```

-continued

```
<400> SEQUENCE: 20
tcacttatcg tcatcgtcct tctagtctag atataaaggt tttacatagt tg          52

<210> SEQ ID NO 21
<211> LENGTH: 20
<212> TYPE: DNA
<213> ORGANISM: Homo sapiens

<400> SEQUENCE: 21
aattcccggg tatcgcatcg                                              20

<210> SEQ ID NO 22
<211> LENGTH: 20
<212> TYPE: DNA
<213> ORGANISM: Homo sapiens

<400> SEQUENCE: 22
gatccgatgc gatacccggg                                              20

<210> SEQ ID NO 23
<211> LENGTH: 28
<212> TYPE: DNA
<213> ORGANISM: Artificial Sequence
<220> FEATURE:
<223> OTHER INFORMATION: Primer Sequence

<400> SEQUENCE: 23
gactacaagg acgatgacga taagtagc                                     28

<210> SEQ ID NO 24
<211> LENGTH: 37
<212> TYPE: DNA
<213> ORGANISM: Artificial Sequence
<220> FEATURE:
<223> OTHER INFORMATION: Primer Sequence

<400> SEQUENCE: 24
ggccgctact tcatcgtcat cgtccttgta gtctgca                           37

<210> SEQ ID NO 25
<211> LENGTH: 44
<212> TYPE: DNA
<213> ORGANISM: Homo sapiens

<400> SEQUENCE: 25
atggactaca aggacgatga cgataagagc ggcggcgggc cttc                   44

<210> SEQ ID NO 26
<211> LENGTH: 20
<212> TYPE: DNA
<213> ORGANISM: Homo sapiens

<400> SEQUENCE: 26
tcaggaggag ttagtgaggg                                              20
```